United States Patent [19]

Pfirmann et al.

[11] Patent Number: 5,849,959
[45] Date of Patent: Dec. 15, 1998

[54] DERIVATIVES OF 2, 3, 6-TRIFLUOROPHENOLS AND A PROCESS FOR THEIR PREPARATION

[75] Inventors: Ralf Pfirmann, Griesheim; Rainer Wingen, Hattersheim, both of Germany

[73] Assignee: Clariant GmbH, Germany

[21] Appl. No.: 763,758

[22] Filed: Dec. 11, 1996

[30] Foreign Application Priority Data

Dec. 13, 1995 [DE] Germany .................. 195 46 520.2

[51] Int. Cl.$^6$ .................................................. C07C 41/00
[52] U.S. Cl. .................. 568/647; 568/631; 568/635; 568/656; 568/731; 568/774; 568/775; 568/776
[58] Field of Search ................................... 568/731, 774, 568/775, 776, 631, 635, 647, 656

[56] References Cited

U.S. PATENT DOCUMENTS

| | | |
|---|---|---|
| 4,831,190 | 5/1989 | Ataka et al. . |
| 5,446,198 | 8/1995 | Pfirmann et al. . |
| 5,525,258 | 6/1996 | Wingen et al. . |

FOREIGN PATENT DOCUMENTS

| | | |
|---|---|---|
| 0271275 | 11/1991 | European Pat. Off. . |
| 0 602 596 | 6/1994 | European Pat. Off. . |
| 0602549 | 6/1994 | European Pat. Off. . |
| 0602596 | 6/1994 | European Pat. Off. . |
| 42 34 585 | 8/1994 | Germany . |

OTHER PUBLICATIONS (Abstract) Ramanan et al., Indian Drugs (1985), 23(2), 105–107, 1985.

Burdon, "Aromatic Polyfluoro–Compounds. Part XVI", J, J. Chem. Soc., London, pp. 6326–6328 (Nov. 1965).

Wray, Victor et al., "Additivity of Substituent Effects Upon Proton–Fluorine Coupling Constants in Polysubstituted Fluorobenzenes", J. Chem. Cos. Perkin II, London, pp. 1307–1312, (1976).

March, J.: *Advanced Organic Chemistry*, fourth edition, 1992, pp. 563–565.

Greene, T., "Aromatic Ethers", Chapter 3, *Protective Groups in Organic Chemistry*, N.Y., John Wiley and Sons, 1991, pp. 143–174.

Primary Examiner—Michael L. Shippen
Attorney, Agent, or Firm—Connolly & Hutz

[57] ABSTRACT

The present invention relates to compounds of the formula (1)

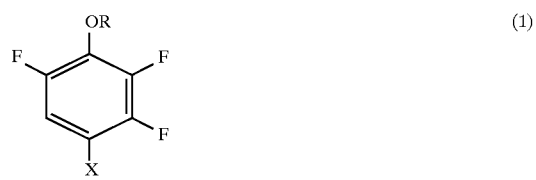

(1)

where R is H, a straight-chain or branched alkyl radical with 1 to 6 carbons, a fluorinated straight-chain or branched alkyl radical with 1 to 6 carbons, a benzyl radical, or a benzyl radical substituted by an alkyl group or alkoxy group with 1 to 4 carbons each, or by halogen, X is H, Cl, Br or I, and X is different from R, and a process for their preparation.

18 Claims, No Drawings

DERIVATIVES OF 2, 3, 6-TRIFLUOROPHENOLS AND A PROCESS FOR THEIR PREPARATION

The present invention relates to novel benzenes fluorinated in 2,3,6-position, which are derived from 2,3,6-trifluorophenol. These novel compounds are of particular importance for the preparation of liquid crystals with favorable properties. They can be converted into the liquid-crystalline compounds with favorable properties as described in EP 0602596.

Owing to the importance of liquid-crystalline compounds, for example in the context of data processing or graphic presentation of texts and drawings, it is a worthwhile object to make available novel compounds suitable for the preparation of liquid crystals with favorable properties.

This object is achieved by compounds of the formula (1)

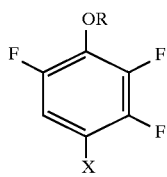

(1)

where R is H, a straight-chain or branched alkyl radical with 1 to 6 carbons, a fluorinated straight-chain or branched alkyl radical with 1 to 6 carbons, a benzyl radical, or a benzyl radical substituted by an alkyl group or an alkoxy group with 1 to 4 carbons each, or by halogen, X is H, Cl, Br or I, and X is different from R.

Owing to their substitution at the 1,2,3,6-position or 1,2,3,4,6-position, the novel compounds have an unusual substitution pattern.

In compounds of the formula (1), R is in particular H, a straight-chain or branched alkyl radical with 1 to 6 carbons, or a benzyl radical, preferably a straight-chain or branched alkyl radical with 1 to 4 carbons or a benzyl radical, especially preferably an alkyl radical with 1 to 2 carbons or a benzyl radical.

In compounds of the formula (1), X is in particular H, Cl or Br, preferably H or Br, especially preferably Br.

Of particular interest are compounds of the formula (1)

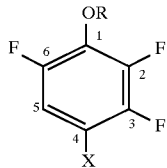

(1)

where R is a methyl or benzyl radical, and X is H, Cl, Br or I, especially H, Cl or Br. These are 2,3,6-trifluoroanisole and 2,3,6-trifluorobenzyloxybenzene and their 4-halogenated derivatives. Also of particular interest are compounds of the formula (1) where R is H and X is Cl, Br or I, especially where R is H and X is Br. These include 4-chloro-2,3,6-trifluorophenol, 4-bromo-2,3,6-trifluorophenol and 2,3,6-trifluoro-4-iodophenol.

Since there is no process for the preparation of the novel derivatives of 2,3,6-trifluorophenol, there is an urgent need to make available a suitable process for their preparation whereby the desired products become available in high yield in a technically simple manner.

This object is achieved by a process for the preparation of the compounds of the formula (1), where R and X have the abovementioned meanings. It comprises decarboxylating a compound of the formula (2)

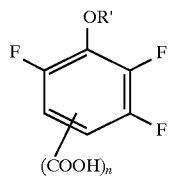

(2)

where R' has the same meanings as R, or, alternatively, is H and n=1 or 2, in a basic solvent or solvent mixture in the presence of a decarboxylation catalyst at 120° to 220° C., where optional acidifying the reaction mixture, separating off the decarboxylated product, and where optional introducing into the decarboxylated product the radical X=Cl, Br or I, by halogenation, and where optional the radical R, if it is not H, by etherification.

In many instances it is advantageous to employ a compound of the formula (2) where R' has the same meanings as R.

The decarboxylation of polyhalogenated or, more precisely, polyfluorinated benzoic acids proceeds unforeseeably highly variably and affords the corresponding decarboxylated products in greatly differing yields. Whereas the decarboxylation of 2,3,4,5-tetrafluorobenzoic acid affords 1,2,3,4-tetrafluorobenzene in 60 to 62% yield, the decarboxylation of 2-chloro-4,5-difluorobenzoic acid only gives a yield of 1% of 1-chloro-3,4-difluorobenzene (see also N. J. O'Reilly, ACS 10$^{th}$ Winter Fluorine Symposium, St. Petersburg, Florida 1991).

Against this background, it is surprising that the decarboxylation of the compounds of the formula (2) gives the corresponding decarboxylated products in yields of 65 to 90%. It has to be particularly taken into account in this context that the carboxylic acids of the formula (2) have, with respect to the fluorine substituents, a substitution pattern very much like the substitution pattern of the halogens in 2-chloro-4,5-difluorobenzoic acid. In both instances, the three fluorine or halogen radicals, respectively, are arranged in an unsymmetrical way on the benzene ring, as is evident for example from the following formulae (A), (B) and (C):

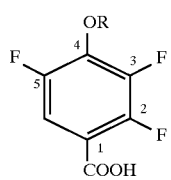

(A)

Benzoic acid of the formula (2)

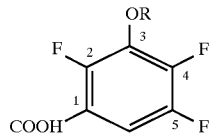

(B)

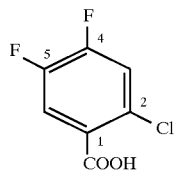

(C)

2-Chloro-4, 5-difluorobenzoic acid

In the compound of the formula (A), the fluorine substituents are arranged in 2,3,5-position, whereas in the compound of the formula (B), the fluorine atoms have the same arrangement as the halogens in 2-chloro-4,5-difluorobenzoic acid and accordingly occupy the 2,4,5-position.

The starting materials of the formula (2) needed for the preparation of the compounds of the formula (1) according to the invention can be prepared as described in EP 602 549 or EP 271 275.

The process according to the invention can be carried out with particular success using a compound of the formula (2) where n=1.

In general, a basic and dipolar aprotic solvent, an alkylamine with 6 to 30 carbons, a dialkylamine with 6 to 30 carbons per alkyl radical, a trialkylamine with 4 to 30 carbons per alkyl radical, an N-containing heterocyclic compound, or a mixture thereof is used as basic solvent or solvent mixture.

Suitable basic dipolar aprotic solvents are N-methylpyrrolidone, dimethylacetamide and 1,3-dimethylimidazolidin-2-one, or mixtures thereof.

In a number of instances it is advantageous to employ an alkylamine with 8 to 20 carbons, a dialkylamine with 8 to 20 carbons per alkyl radical, a trialkylamine with 6 to 20 carbons per alkyl radical, in particular an alkylamine with 8 to 14 carbons, a dialkylamine with 8 to 16 carbons per alkyl radical, a trialkylamine with 6 to 14 carbons per alkyl radical or mixtures thereof. N-containing heterocyclic compounds used are pyridine, an alkylated pyridine, quinoline, an alkylated quinoline, isoquinoline, an alkylated isoquinoline, or mixtures thereof.

A variant of the process comprises using a basic solvent and water as solvent mixture.

The decarboxylation catalyst used is copper, a copper(I) compound, a copper(II) compound, for example copper(I) oxide, copper(II) oxide, copper(I) sulfate, copper(II) sulfate, copper(I) chloride, copper(II) chloride, copper(I) fluoride, copper(II) fluoride, copper carbonate, copper(I) hydroxide or copper(II) hydroxide.

The decarboxylation catalyst is employed in amounts of 0.1 to 10%, in particular 0.3 to 3%, by weight based on the compound of the formula (2).

In a number of instances it is advantageous to carry out the decarboxylation at a pH of 5 to 8. This applies in the case where the pH can be measured, for example if water-containing solvents are used.

The decarboxylation can be carried out with good results at a temperature of 130° to 190° C., in particular 140° to 170° C.

After the decarboxylation has ended, the reaction mixture is acidified, for example by adding a mineral acid such as hydrochloric acid, sulfuric acid, or phosphoric acid, and the decarboxylated product is separated off by extraction or steam distillation. In some instances steam distillation has been found to be a particularly gentle method of separation.

Acidification is necessary when the compounds of the formula (1) present in the reaction mixture have acidic groups. Acidification of the reaction mixture can be omitted when the compound of the formula (1) does not contain any acidic groups, for example when R is not H.

If it is intended to separate off the decarboxylated product by extraction, a water-insoluble organic solvent or solvent mixture is used. Suitable solvents are chlorinated aliphatic hydrocarbons, for example dichloromethane, chloroform, 1,2-dichloroethane, trichloroethylene, perchloroethylene, aromatic hydrocarbons, for example toluene, o-xylene, m-xylene, p-xylene, mixtures of isomeric xylenes, mesitylene, chlorobenzene, dichlorobenzene, isomeric dichlorobenzenes, dichlorotoluene, chlorotoluene, or mixtures thereof. Also suitable are aliphatic hydrocarbons, for example n-pentane, n-hexane, n-heptane, their isomers, gasolines, petroleum ethers, or mixtures thereof.

If the decarboxylated product, for example lower ethers of 2,3,6-trifluorophenol or the 2,3,6-trifluorophenol needed as a precursor for a subsequent halogenation or etherification, is to be separated off by steam distillation, then water may be added to the decarboxylated product, and the water-containing mixture obtained may be distilled, or steam may be introduced into directly and the desired product distilled over with the steam. Steam distillation has the advantage that the decarboxylated product is obtained in prepurified form and, in most instances, does not require further purification.

The radical X=Cl, Br or I is introduced by halogenation of the decarboxylated product. The halogenation may be carried out in substance, i.e. in the absence of a solvent, or in the presence of a solvent. Suitable solvents are organic solvents inert under the conditions of the halogenation, and water. Suitable organic solvents are aliphatic hydrocarbons, for example hexane, heptane, octane, halogenated aliphatic hydrocarbons, for example dichloromethane, chloroform, dichloroethane, perchloroethylene, or halogenated aromatic hydrocarbons, for example chlorobenzene, dichlorobenzene, mixtures of isomeric dichlorobenzenes, trichlorobenzene, mixtures of isomeric trichlorobenzenes and chlorotoluene, dichlorotoluene, trichlorotoluene and their isomeric mixtures. Mixtures of the abovementioned solvents may also be used.

The halogenation may be carried out in the presence of a halogenation catalyst. Suitable halogenation catalysts are for example iron, iron(II), iron(III) halides, iodine, or iodine halides, and their mixtures. Although the aromatic ring in the decarboxylated product might have been expected to be deactivated considerably owing to the three fluorine atoms present on the aromatic ring, the decarboxylated product proves to be surprisingly reactive. In fact, it is possible to carry out the halogenation even in the absence of a halogenation catalyst. This variant of the halogenation is usually preferred.

As halogenating agent, the halogen can be used in elemental form or as hypohalite. The halogenation is particularly simple when using hypohalite, for example in the form of a halogen bleach, especially chlorine bleach or bromine bleach. The halogen is used in an amount of 80 to 200%, in particular 100 to 120%, of the stoichiometrically required amount, and the halogenation is carried out at a temperature of −10° to 80° C., in particular 0° to 50° C., preferably 10° to 40° C.

The concentration in organic solvents and/or water of the decarboxylated product used as starting material can be varied over a wide range.

It is favorable when working in an aqueous medium, especially when using 2,3,6-trifluorophenol, but also with other decarboxylated products, to work in the presence of 1 to 10, in particular 2 to 5, mole equivalents of hydroxide, based on 2,3,6-trifluorophenol or decarboxylated product. Hydroxide sources may be solutions of alkali metal or alkaline earth metal hydroxides, or substances acting as a base.

The radical R may be introduced by etherification, provided R is not H. For this purpose, the decarboxylated product can be reacted in the form of its phenolate with a halogen compound R-Hal according to Williamson's ether synthesis, or with a sulfate of the formula R—O—SO$_2$—O—R. See also T. Greene, Protective Groups in Organic Chemistry (1991) (John Wiley & Sons) Chapter Aromatic Ethers, pages 143 to 174.

When carrying out the process according to the invention, there are no restrictions with regard to the order of halogenation and etherification of the decarboxylated product. If desired, only the halogenation or only the etherification is carried out. It is also possible to carry out the halogenation initially, and then the etherification, or, conversely, first the etherification and then the halogenation.

It is possible to dispense with etherification and optionally halogenation when a compound of the formula (2) where R' has the same meanings as R in the formula (1), but is not H, is used in the process according to the invention, and is just decarboxylated. In these instances, the decarboxylated product already has an ether substituent. If desired, this product may subsequently be halogenated.

The process may be carried out continuously or batchwise at atmospheric pressure, reduced pressure or superatmospheric pressure.

The Examples which follow illustrate the invention without restricting it thereto.

EXPERIMENTAL PART:

Example 1a

Preparation of 2,3,6-trifluorophenol (precursor)

74.2 g (0.386 mol) of colorless to light beige 4-hydroxy-2,3,5-trifluorobenzoic acid (prepared according to EP 602 549) are dissolved in 350 g of N-methylpyrrolidone, 1 g of copper(I) oxide is added, and the mixture is heated with stirring at 155° C. for 3 hours. After the steady evolution of gas has ended, stirring is continued for 1 hour at up to a temperature of 170° C.

After cooling, 500 g of water and 200 g of 96% strength sulfuric acid are added to the mixture, and the decarboxylated product is distilled off with water. Because of the high water solubility of 2,3,6-trifluorophenol, only a small organic phase is formed. The distillate is extracted with 100 g portions of dichloromethane, and the aqueous phase which has been freed of the product of value is recycled into the distillation. This procedure is repeated (6 to 8 times) until no significant proportion of product can be detected in the still bottom. The combined organic phases are dried over magnesium sulfate and filtered, and the dichloromethane is removed using a rotary evaporator. 56 g (equivalent to 73% yield) of a yellow-orange oil containing about 25% of N-methylpyrrolidone (GC analysis) are obtained.

The crude product is worked up together with the crude product obtained from Example 1b.

Example 1b

Preparation of 2,3,6-trifluorophenol (precursor)

144.1 g (0.75 mol) of 4-hydroxy-2,3,5-trifluorobenzoic acid (prepared according to EP 602 549) are dissolved in 500 g of N-methylpyrrolidone, 2 g of copper(I) oxide are added, and the mixture is heated with stirring to 155° C. According to HPLC analysis, complete conversion has not been achieved after 3 hours. 250 g of N-methylpyrrolidone, 4 g of copper(I) oxide and 2.5 g of water are added, and heating with vigorous stirring at 180° C. is continued for a further 3.5 hours. After this, no 4-hydroxy-2,3,5-trifluorobenzoic acid can be detected in the reaction mixture. The dark red suspension is cooled and poured onto a mixture of 1000 g of water and 185 g of 30% strength by weight hydrochloric acid (equivalent to 1.5 mol). The mixture is extracted 5 times with 100 g of dichloromethane each time, the combined organic phases including the crude product obtained from Example 1a are washed with 2 times 50 g of water and dried over magnesium sulfate, and the dichloromethane is removed using a rotary evaporator. 126 g of crude, yellow-orange 2,3,6-trifluorophenol which is already of 95% purity according to GC analysis are obtained.

This crude product is fractionally distilled using a Vigreux column of 25 cm length by adding diphenyl sulfone to the still bottom. At 8 Torr (11.4 mbar) and 98° to 110° C. top-of-column temperature, 114.5 g (0.774 mol) of 2,3,6-trifluorophenol (equivalent to a yield based upon the two Examples 1a and 1b of 68%) are obtained as colorless oil, which solidifies to give an extremely volatile, colorless solid melting at about 40° C., with a strong tendency to sublimation. The temperature in the still bottom passes through a temperature interval of 120° to 160° C. during distillation.

MS: m/z (%)*=44, 49, 50 (17.3), 51 (5.3), 53, 55, 56 (5.9), 57 (4.8), 60, 61 (3.8), 62, 63, 64, 68 (4.3), 69 (10.2), 70 (2.4), 71 (2.7), 73, 74 (5.2), 75 (8.9), 77, 79 (2.7), 80 (3.9), 81 (12.7), 82, 86, 87, 88, 91, 93 (3.6), 94, 98, 99 (39.8), 100 (73.4), 101 (7.7), 117, 119 (15.0), 120, 128 (13.1), 129, 147 (2.9), 148 (100), 149 (6.9).

* Peaks without any percentages specified are in the range of 0.6 to 1.9% each; 2,3,6-Trifluorophenol; $^1$H-NMR (CDCl$_3$, TMS); δ[ppm]=5.24 (s(br), 1H—OH); 6.69 (cm, 1H, Ar—H$^4$); 6.84 (cm, 1H, Ar—H$^5$); $^{19}$F-NMR (CDCl$_3$, CFCl$_3$); δ[ppm]=−141.25 (m, 1F, ArF$^6$); −141.74 (dddd, 1F, J=7.6 Hz; 9.2 Hz, 13.7 Hz, 19.8 Hz, Ar—F$^3$); −157.74 (dddd, 1F, J=7.6 H, 19.9 Hz, Ar—F$^2$).

Example 2

Preparation of 2,3,6-trifluoroanisole 100 g (0.485 mol) of 3-methoxy-2,4,5-trifluorobenzoic acid (prepared by alkylation of 3-hydroxy-2,4,5-trifluorobenzoic acid), 60 g of N-methyl-pyrrolidone and 0.5 g of copper(I) oxide are initially charged, and the red mixture is heated with stirring at 160° to 166° C. for 1.5 hours. The end of the evolution of gas and HPLC analysis indicate complete conversion. Subsequent distillation at normal pressure affords about 50 g of a colorless liquid. The still bottom is discarded.

The aqueous phase of the distillate (residual water from N-methyl-pyrrolidone) is extracted with 10 g of dichloromethane and combined with the organic phase, and the entire organic phase is then washed with 50 ml of water to remove N-methylpyrrolidone. The organic phase is dried and filtered, and remaining solvent fractions are removed. 58 g (0.358 mol) of colorless 2,3,6-trifluoroanisole of a purity of 95% (according to GC analysis) are obtained. This is equivalent to a yield of 70%. MS: m/z (%)*=49, 50 (3.5), 51 (4.2), 55, 56 (2.7), 57 (3,9), 61 (3.3), 62 (2.8), 63 (3.0), 68 (3.9), 69 (12.2), 71, 74 (2.5), 75 (9.3), 79, 80 (3.2), 81 (17.7), 82, 83, 84 (2.6), 86, 87, 88, 92, 93 (7.2), 95, 98, 99 (9.8), 100 (3.5), 101, 111, 112, 113(4.6), 114(3.3), 115, 117, 119(100), 120(6.0), 128, 130, 131 (6.8), 132 (2.6), 133 (3.5), 147 (61.5), 148 (4.6), 159, 162 (99.5), 163 (8.3).

Peaks without percentages<2% 2,3,6-Trifluoroanisole: $^1$H-NMR (CDCl$_3$, TMS): δ[ppm]=4.04 (ct, 3H, Ar—OCH$_3$); 6.74–6.88 (m, 2H, Ar—H$^{4,5}$); $^{19}$F-NMR (CDCl$_3$, CFCl$_{13}$): δ[ppm]=−134.25 (cm, 1F, Ar—F$^6$); −141.6 (dddd, 1F, Ar—F$^3$); −152.15 (dcm, 1F, Ar—F$^2$);

Example 3

Preparation of 4-chloro-2,3,6-trifluorophenol 10 g (0.0678 mol) of 2,3,6-trifluorophenol (prepared according to Examples 1a and 1b) are dissolved in 50 ml of dichloromethane, and this solution is admixed at 20° C. with 20 g of 30% strength aqueous sodium hydroxide solution. 60 g of a 14.8% strength chlorine bleach (0.119 mol, determined by titration), which is prepared from 100 g of NaOH, 240 g of water and 57 g of chlorine, are then added, and the solution is stirred vigorously at 20° C. for 48 hours. Excess chlorine bleach is then destroyed by the addition of sodium dithionite, the reaction mixture is acidified to pH=2, and the organic phase containing the 4-chloro-2,3,6-trifluorophenol is separated off and dried over $MgSO_4$.

After filtration and removal of solvent, 10.2 g of crude product are obtained, which contains 4-chloro-2,3,6-trifluorophenol of a purity of>93% as determined by GC analysis, equivalent to 55.9 mmol. This is equivalent to a yield of 82.5%, based upon the 4-chloro-2,3,6-trifluorophenol employed.

Example 4
Preparation of 4-bromo-2,3,6-trifluorophenol 10 g (0.0678 mol) of 2,3,6-trifluorophenol (prepared according to Examples 1a and 1b) are dissolved in 50 ml of dichloromethane, and this solution is admixed at 20° C. with 13 g (0.0811 mol) of bromine. After mixing by shaking, the mixture is left standing for 7 days.

The conversion, based on the 2,3,6-trifluorophenol employed, is, according to GC analysis, more than 95%, with about 10% dibromination occurring.

The mixture is deacidified by the addition of 5% strength aqueous sodium hydrogen carbonate solution. The organic phase is separated off and dried over $MgSO_4$. The mixture obtained is freed of solvent using a rotary evaporator, and the remaining residue (16.6 g) is fractionally distilled using a Vigreux column of 30 cm length.

At 5 Torr (6.7 mbar) and a top-of-column temperature of 68° to 75° C., 10.8 g (0.0472 mol) of 4-bromo-2,3,6-trifluorophenol of a purity of 95%, as determined by GC analysis, are obtained. This is equivalent to a yield of 70.2%, based on 2,3,6-trifluorophenol employed. During the distillation, the still bottom temperature goes from 105° to 190° C.

4-Bromo-2,3,6-trifluorophenol; $^1$H-NMR ($CDCl_3$, TMS): δ[ppm]=5.4((br), 1H, Ar—OH); 7.13 (ddd, 1H, $J_{AD}$=2.8 Hz, $J_{AB}$=6 Hz, $J_{AC}$=9.7 Hz, Ar—$H^5$ (A)); $^{19}$F-NMR ($CDCl_3$, $CFCl_3$): δ[ppm]=−133.65 (ddd, 1F, $J_{AB}$=6 Hz, $J_{BC}$=10.4 Hz, $J_{BD}$=21.3 Hz, Ar—$F^3$ (B)); −139.76 (ddd, 1F, $J_{CD}$=6.9 Hz, $J_{AC}$=9.7 Hz, $J_{BC}$=10.4 Hz, Ar—$F^5$ (C)); −154.31 (ddd, 1F, $J_{AD}$=2.8 Hz, $J_{CD}$=6.9 Hz, $J_{BD}$=21.3 Hz, Ar—$F^4$ (D)); IR: ν [$cm^{-1}$]=720, 825, 850, 985, 1080, 1190, 1230, 1320, 1350, 1480, 1510, 1615, 3080, 3430 (br), 3570; MS: m/z (%)=49, 50, 51 (2.7), 55, 56 (3.3), 61 (2.8), 68 (6.1), 69 (10.2), 71 (2.6), 74, 75 (6.7), 79 (7.3), 80 (7.3), 81 (3.3), 87, 93 (3.5), 98 (4.5), 99 (53.1), 100 (3.5), 113, 114, 117 (2.7), 118 (5.3), 119 (15.5), 130, 146, 147 (3.5), 178 (20.6), 179 (2.0), 180 (20.8), 181, 197 (4.8), 199 (5.2), 206 (4.0), 208 (5.3), 226 (92.7), 227 (8.4), 228 (100), 229 (6.4)

Example 5
Preparation of 2,3,6-trifluoroisopropoxybenzene

At 20° to 25° C., 14.3 g (0.1 mol) of 2,3,6-trifluorophenol (prepared according to Examples 1a and 1b) and 200 ml of dimethylformamide are initially charged, and 27.5 g (0.194 mol) of granulated potassium carbonate (99% pure) and 42.3 g (0.344 mol) of 2-bromopropane (99% pure) are added at this temperature with stirring. A colorless suspension is formed, which, after 3 hours, contains 2,3,6-trifluoroisopropoxybenzene corresponding to a conversion of 94% (determined by GC analysis) and displays a pink color. Stirring is continued overnight (20 hours), and the entire mixture is added to 400 g of water. Giving off a little heat, a lower pink-colored organic phase containing the product of value settles. The phases are separated, and the water phase is extracted two times with 30 ml of dichloromethane each time. The dichloromethane phase and the organic phase are combined, dried over $Na_2SO_4$ and filtered. The solvents are then removed using a rotary evaporator.

By fractional distillation, three fractions (a total of 13.5 g, equivalent to 71 mmol) of 2,3,6-trifluoroisopropoxybenzene (mean degree of purity 94.2%, as determined by GC analysis) are obtained.

2,3,6-Trifluoroisopropoxybenzene; MS: m/z (%)=27 (7.0), 31, 38, 39 (7.4), 40, 41 (11.1), 42 (2.1), 43 (9.2), 50 (2.4), 51 (2.6), 57, 69 (4.5), 75 (3.6), 81 (5.4), 93, 99 (5.5), 100 (13.9), 101, 119 (14.0), 127, 128 (4.4), 131 (2.2), 148 (100), 149 (7.3), 175 (6.9), 190; ($M^+$; 4,7); $^1$H-NMR ($CDCl_3$, TMS); δ[ppm]=1.36 (d, 6H, —OCH($CH_3$)$_2$); 4.49 (tr/hpt, 1H, ArOCH—); 6.82 (m, 2H, Ar—$H^{4,5}$); $^{19}$F-NMR ($CDCl_3$, $CFCl_3$) δ[ppm]=−132.80 (m,1F, J=4.6 Hz; 13.0 Hz, Ar—$F^6$); −141.80 (dddd, 1F, J=13.0 Hz; 20.4 Hz, Ar—$F^3$); −150.40 (dm, 1F, J=4.6 Hz, 20.4 Hz, Ar—$F^2$);

Example 6
Preparation of 1,3,4-trifluoro-2-(2'-fluorobenzyloxy) benzene

Under an atmosphere of argon, 200 ml of N,N-dimethylformamide, 27.5 g (0.194 mol) of potassium carbonate, 14.3 g (0,1 mol) of 96.8% pure 2,3,6-trifluorophenol (prepared according to Examples 1a and 1b) and 49.7 g (0.344 mol) of 2-fluorobenzyl chloride are initially charged with stirring at 20° to 25° C. The initially colorless suspension takes on a color. After two hours, the now beige-brown suspension no longer contains any 2,3,6-trifluorophenol (as determined by GC analysis).

After 5.5 hours, the entire mixture is added to 400 g of water, and a turbid, brown organic phase settles. The organic and aqueous phases are separated, and the aqueous phase is extracted two times with 40 ml of dichloromethane each time. The organic phase obtained contains 53% of dimethyformamide, 35% of 2-fluorobenzyl chloride, and only 13% of 1,3,4-trifluoro-2-(2'-fluorobenzyloxy)benzene. Because of the low amount of products of value, this organic phase is not processed any further. The organic phase that separated off earlier with the addition of water is washed two times with 30 g of water each time, separated off from the aqueous phase, and dried over $Na_2SO_4$.

By fractional distillation at 1 to 2 Torr (1.3 to 2.6 mbar) and 39° C. top-of-column temperature, 24.3 g of 2-fluorobenzyl chloride are recovered. Subsequently, 7.7 g (40% of 2-fluorobenzyl chloride, 60% of 1,3,4-trifluoro-2-(2'-fluorobenzyloxy)benzene) are obtained as a mixed fraction, which, like the pure product (99%, as determined by GC analysis), passes over at 1 to 2 Torr (1.3 to 2.6 mbar) and a top-of-column temperature of 104° C. 20.1 g (78.5 mmol equivalent to 78.5% yield) of 1,3,4-trifluoro-2-(2'-fluorobenzoyloxy)benzene are obtained as a colorless oil. Including the mixed fraction obtained as intermediate cut, the yield is 24.7 g (96.5 mmol equivalent to 96.5% yield).

A still bottom of 1 g remains.

MS: m/z (%)=28, 31 (2.2), 38, 39 (4.7), 43, 50, (2.8), 51 (3.9), 56, 57 (7.5), 58, 59 (2.1), 61, 62 (2.3), 63 (5.4), 68, 69 (4.1), 70, 74, 75 (3.7), 80, 81 (4.6), 83 (21.5), 84, 88, 89 (2.8), 93, 95, 99, 100, 107 (4.6), 109 (100), 110 (8.6), 119 (9.9), 120, 123, 131, 147 (1.7), 206 (0.2), 256 ($M^+$, 1.9), 257; $^1$H-NMR ($CDCl_3$, TMS); δ[ppm]=5.28 (s, 2H, Ar—O—$CH_2$—Ar); 6.78–6.86 (m, 2H); 7.06 (tm, 1H); 7.15 (tm, 1H); 7.28–7.38 (m, 1H); 7.50 (tm, 1H); $^{19}$F-NMR ($CDCl_3$, $CFCl_3$); δ[ppm]=−118.90 (m, 1F, J=1.5 Hz; 1.5 Hz, Ar—$F^{2'}$); −132.80 (m, 1F, J=3.8 Hz; 1.5 Hz; 13.0 Hz, Ar—$F^6$); −141.40 (cm, 1F, J=13.0 Hz; 20.2 Hz, Ar—$F^3$); −150.50 (m, 1F, J=1.5 Hz; 3.8 Hz, 20.2 Hz, Ar—$F^2$);

Example 7
Preparation of 2,3,6-trifluorophenol (precursor) starting from 4-hydroxy-3,5,6-trifluorophthalic acid a) Preparation of 3-hydroxy-2,4,5-trifluorobenzoic acid (precursor)

450.3 g of a strongly alkaline, aqueous solution containing 41.8 g (0.177 mol) of 4-hydroxy-3,5,6-trifluorophthalic acid in the form of the corresponding alkali metal salts, and 0.4 g of copper(I) oxide are admixed with 12.6 g of a mixture of various aliphatic trialkylamines with 6 to 14 carbons each in the alkyl radical (Hostarex A 327; a commercial product of Hoechst AG), and adjusted to pH 5 with in total 166.8 g of 30% strength aqueous hydrochloric acid, and subsequently heated to 105° C. with stirring over 6 hours. The pH changes due to decarboxylation, and is appropriately corrected (adjusted to pH 5) after one hour by addition of 23.4 g of 30% strength aqueous hydrochloric acid and after 3 hours by addition of 15.9 g of 30% strength aqueous hydrochloric acid. After cooling, the pH is adjusted to 8, and the aqueous phase (601 g) containing 31.3 g (91.3% of theory) of 3-hydroxy-2,4,5-trifluorobenzoic acid (as determined by calibrated HPLC chromatography) is separated off. The aqueous phase is then adjusted to a pH of 1 to 2 and extracted continuously, for example with tert-butyl ether or butyl acetate. From the organic phase, after drying, filtration and removal of solvent, 38.3 g of a viscous, oily residue are obtained, which slowly crystallizes.

b) Preparation of 2,3,6-trifluorophenol (precursor)

The residue (38.3 g) obtained according to Example 7a is initially charged together with 150 g of N-methylpyrrolidone and 0.4 g of copper(I) oxide with stirring, and heated at 150° to 160° C. for 3.5 hours. The 3-hydroxy-2,4,5-trifluorobenzoic acid employed decarboxylates, forming 2,3,6-trifluoro-phenol. Subsequent workup by extraction with dichloromethane as described in Example 1b gives, after removal of solvent, 14.7 g of a crude, orange-colored oil, which contains, as determined by GC analysis, 94% of 2,3,6-trifluorophenol (0.093 mol equivalent to 57% yield, based on the 3-hydroxy-2,4,5-trifluorobenzoic acid prepared as an intermediate according to Example 7a).

What is claimed is:

1. A compound of the formula (1):

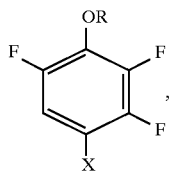

(1)

where
(a) R is a benzyl radical or a benxyl readical substituted by an alkyl or alkoxy group having 1 to 4 carbons each, or by a halogen atom, and X is H, Cl, Br or I; or
(b) is an isopropyl group and X is H, Cl, Br or I.

2. A compound of the formula (1):

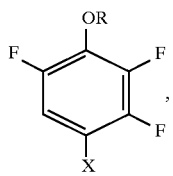

(1)

where
R is H and X is Cl, Br or I.

3. A process for the preparation of a compound of the formula (1) as claimed in claim 1, where R and X have the above-mentioned meanings, which comprises decarboxylating a compound of the formula (2)

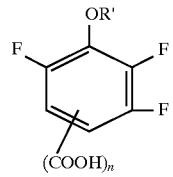

where R' has the same meanings as R, or, alternatively, is H and n=1 or 2, in a basic solvent medium in the presence of a decarboxylation catalyst at 120° to 220° C., optionally acidifying the reaction mixture, separating off the decarboxylated product, and optionally introducing into the decarboxylated product the radical X=Cl, Br or I by halogenation, and, when the radical R is not H, introducing said radical R by etherification.

4. A process as claimed in claim 3, wherein R' in the compound of the formula (2) to be decarboxylated has the same meanings as R.

5. A process as claimed in claim 3, wherein n in the compound of the formula (2) to be decarboxylated is 1.

6. A process as claimed in claim 3, wherein the basic solvent medium is a single solvent or solvent mixture and is a basic dipolar aprotic solvent, an alkylamine with 6 to 30 carbons, a dialkylamine with 6 to 30 carbons per alkyl radical, a trialkylamine with 4 to 30 carbons per alkyl radical, an N-containing heterocyclic compound, or a mixture thereof.

7. A process as claimed in claim 6, wherein the basic dipolar aprotic solvent is N-methylpyrrolidone, dimethylacetamide, or 1,3-dimethylimidazolinin-2-one or a mixture thereof.

8. A process as claimed in claim 6, wherein the single solvent or solvent mixture is an alkylamine with 8 to 20 carbons, a dialkylamine with 8 to 20 carbons per alkyl radical, a trialkylamine with 6 to 20 carbons per alkyl radical or a mixture thereof.

9. A process as claimed in claim 6, wherein the N-containing heterocyclic compound is pyridine, an alkylated pyridine, quinoline, an alkylated quinoline, isoquinoline, an alkylated isoquinoline, or a mixture thereof.

10. A process as claimed in claim 3, wherein the basic solvent medium comprises a mixture comprising a basic solvent and water.

11. A process as claimed in claim 3, wherein the decarboxylation catalyst is copper, a copper(I) compound or a copper(II) compound.

12. A process as claimed in claim 3, wherein the amount of decarboxylation catalyst is 0.1 to 10%, by weight, based on the compound of the formula (2).

13. A process as claimed in claim 3, wherein the decarboxylating step is carried out at a pH within the range of 5 to 8.

14. A process as claimed in claim 3, wherein the decarboxylating step is carried out at a temperature of 130° to 190° C.

15. A process as claimed in claim 3, wherein the separating step is carried out by extraction or steam distillation.

16. A process as claimed in claim 3, wherein the decarboxylated product is reacted in the presence or absence of a solvent with elemental halogen or a hypohalite in the presence or absence of a halogenation catalyst at 70° to 80° C.

17. A process as claimed in claim 3, wherein the decarboxylated product is obtained initially in the form of a phenolate and is etherified in that form with a halogen compound R-Hal or a sulfate of the formula $(RO)_2SO_2$.

18. A process for the preparation of a compound of the formula (1) as claimed in claim 2, where R and X have the above-mentioned meanings, which comprises decarboxylating a compound of the formula (2)

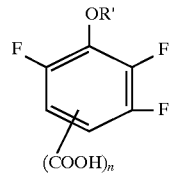

where R' has the same meanings as R, or, alternatively, is H and n=1 or 2, in a basic solvent medium in the presence of a decarboxylation catalyst at 120° to 220° C., optionally acidifying the reaction mixture, separating off the decarboxylated product, and optionally introducing into the decarboxylated product the radical X=Cl, Br or I by halogenation, and, when the radical R is not H, introducing said radical R by etherification.

* * * * *

UNITED STATES PATENT AND TRADEMARK OFFICE
CERTIFICATE OF CORRECTION

PATENT NO. : 5,849,959
DATED : DECEMBER 15, 1998
INVENTOR(S) : PFIRMANN ET AL.

It is certified that error appears in the above-identified patent and that said Letters Patent is hereby corrected as shown below:

Claim 1, line 1 of section (a) (col. 9, line 53), delete "benxyl readical" and insert in its place -- benzyl radical -- ; and Claim 1, line 1 of section (b) (col. 9, line 56), add -- R -- before "is an isopropyl . . ."

Signed and Sealed this

Seventeenth Day of August, 1999

Attest:

Q. TODD DICKINSON

*Attesting Officer*   *Acting Commissioner of Patents and Trademarks*